(12) United States Patent
Dinariev et al.

(10) Patent No.: US 10,309,219 B2
(45) Date of Patent: Jun. 4, 2019

(54) METHOD FOR DETERMINING CHARACTERISTICS OF A GAS-OIL TRANSITION ZONE IN AN UNCASED WELL

(71) Applicant: SCHLUMBERGER TECHNOLOGY CORPORATION, Sugar Land, TX (US)

(72) Inventors: Oleg Yurievich Dinariev, Moscow (RU); Nikolay Vyacheslavovich Evseev, Moscow (RU); Evgey Nikolaevich Ivanov, Moscow (RU)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 0 days.

(21) Appl. No.: 15/299,026

(22) Filed: Oct. 20, 2016

(65) Prior Publication Data
US 2017/0107814 A1    Apr. 20, 2017

(51) Int. Cl.
*E21B 49/08* (2006.01)
*G01N 33/24* (2006.01)
*E21B 47/10* (2012.01)

(52) U.S. Cl.
CPC .......... *E21B 49/088* (2013.01); *E21B 47/10* (2013.01); *G01N 33/241* (2013.01)

(58) Field of Classification Search
CPC ........ E21B 49/08; E21B 49/081; E21B 49/10; E21B 2049/085; E21B 49/088;
(Continued)

(56) References Cited

U.S. PATENT DOCUMENTS

| 4,914,944 A | * | 4/1990 | Herron | G01V 11/00 702/13 |
| 5,306,909 A | * | 4/1994 | Jones | G01N 21/3577 250/255 |

(Continued)

FOREIGN PATENT DOCUMENTS

| RU | 2219337 C1 | 12/2003 |
| RU | 2432450 C2 | 10/2011 |

(Continued)

OTHER PUBLICATIONS

Bassiouni, Z., "Conventional Interpretation Techniques", in Theory, Measurement, and Interpretation of Well Logs, Society of Petroleum Engineers, 1993, Richardson, Texas, USA, pp. 206-224.
(Continued)

*Primary Examiner* — Natalie Huls
*Assistant Examiner* — Mohammed E Keramet-Amircolai

(57) ABSTRACT

In order to determine characteristics of a gas-oil transition zone in a gas capped oil reservoir, samples of a reservoir fluid from a gas and an oil part of the reservoir are taken. To configure an equation of state of hydrocarbon mixtures, reservoir temperature and pressure are measured in places where the samples of the reservoir fluid are taken and densities and compositions of the samples are determined. Porosity, water saturation and total hydrogen content of a saturated rock are measured along the wellbore and a volume and a hydrogen content of hydrocarbon phases are determined. Using the equation of state, density and composition of the hydrocarbon phases are computed and a specific hydrogen content in gas and oil along the wellbore is determined. Gas and oil saturation distribution along the wellbore is determined from the determined specific hydrogen content, determined hydrogen content of the hydrocarbon phases and the measured porosity.

6 Claims, 4 Drawing Sheets

(58) Field of Classification Search
CPC .. G01N 33/2823; G01N 33/24; G01N 33/241; G01V 5/06
USPC ............. 73/152.07, 152.08, 152.09, 152.28
See application file for complete search history.

(56) References Cited

U.S. PATENT DOCUMENTS

| | | | | |
|---|---|---|---|---|
| 2007/0119244 | A1* | 5/2007 | Goodwin | E21B 47/10 73/152.28 |
| 2008/0040086 | A1* | 2/2008 | Betancourt | E21B 49/00 703/10 |
| 2008/0066538 | A1* | 3/2008 | Kamiya | E21B 43/38 73/152.28 |
| 2008/0114547 | A1* | 5/2008 | Syngaevsky | G01V 5/105 702/13 |
| 2010/0064795 | A1* | 3/2010 | Crocker | E21B 49/08 73/152.07 |
| 2010/0175467 | A1* | 7/2010 | DiFoggio | E21B 49/087 73/152.28 |
| 2010/0257926 | A1* | 10/2010 | Yamate | E21B 49/00 73/152.23 |
| 2011/0276271 | A1* | 11/2011 | Dinariev | E21B 43/00 702/8 |
| 2012/0076364 | A1* | 3/2012 | Tjhang | E21B 47/102 382/109 |
| 2012/0232799 | A1* | 9/2012 | Zuo | E21B 49/00 702/6 |
| 2012/0304757 | A1* | 12/2012 | Fujisawa | E21B 49/081 73/152.27 |
| 2013/0046469 | A1* | 2/2013 | Herron | G01N 21/3563 702/2 |
| 2014/0291499 | A1* | 10/2014 | Mathieu | E21B 43/28 250/254 |
| 2014/0360257 | A1* | 12/2014 | Indo | E21B 47/102 73/152.28 |

FOREIGN PATENT DOCUMENTS

| | | |
|---|---|---|
| SU | 630406 A1 | 10/1978 |
| SU | 1314031 A1 | 5/1987 |
| WO | 2004044369 A2 | 5/2004 |

OTHER PUBLICATIONS

Bateman, R. M. "Basic Concepts of Log Analysis", in Open-Hole Log Analysis and Formation Evaluation, Boston, Massachusetts, USA, 1985, pp. 133-146.

Darling, T., "Quicklook Log Interpretation" and "Full Interpretation", in Well Logging and Formation Evaluation, Elsevier, 2005, Boston, Massachusetts, USA, pp. 29-58.

Ellis, D.V. et al., "Lithology and Porosity Estimation" in Well Logging for Earth Scientists. Dordrecht: Springer, 2007, 629-681.

Firoozabadi, A. "Equation of State Representation of Reservoir Fluids Phase Behavior and Properties", in Thermodynamics of Hydrocarbon Reservoirs, New York: McGraw-Hill, 1998, pp. 138-143.

Reid, R. C. et al., "Cubic Equations of State" and "Generalized Benedict-Webb-Rubin Equations", in The Properties of Gases and Liquids New York: Mc-Graw Hill, 1987, pp. 42-47.

Speight, J.G., "Chemical and Composition" and "Fractional Composition", in The Chemistry and Technology of Petroleum. Boca Raton: Taylor & Francis Group, 2007, pp. 177-238.

Speight, J.G., "Fractional Composition" and "Chromatographic Analysis" in Handbook of Petroleum Analysis, New York: John Wiley & Sons, 2001, pp. 223-296.

Tittman, J., "Geological and Petrophysical Interpretation of Logging Measurements", in Geophysical Well Logging. Orlando: Academic Press, 1986, pp. 19-57.

Walas, S. M., "Equations of State" in Phase Equilibria in Chemical Engineering. Boston: Butterworth Publishers, 1985, pp. 54-57.

* cited by examiner

METHOD FOR DETERMINING CHARACTERISTICS OF A GAS-OIL TRANSITION ZONE IN AN UNCASED WELL

CROSS-REFERENCE TO RELATED APPLICATION

This application claims priority to Russian Application No. 2015144873 filed 20 Oct. 2015, which is incorporated herein by reference in its entirety.

BACKGROUND

The disclosure relates to methods of logging wells for gas capped oil reservoirs with a known mineral composition of constituent rocks, that is for oil and gas deposits, in particular, to methods of determining characteristics of a gas-oil transition zone, such as the distribution of gas and oil saturations along a wellbore and a gas-oil capillary pressure.

A gas-oil contact (GOC) is an imaginary surface that separates oil and gas in an oil reservoir, where gas is in a free state and forms a gas cap. The surface of the gas-oil contact is conditional as there is a transition zone of mixed oil-gas saturation between the gas and oil parts of the deposit. Determination of position of the gas-oil contact in geological simulation faces known problems, which are associated with the transition zone structure. In most cases, GOC position is determined from results of fluid inflow tests. In analysis of logging data GOC can be also identified from the abrupt change in the content of hydrogen.

However, there are deposits where geological structure does not allow detecting GOC in the form of a clearly defined surface because there are continuous variations in oil and gas saturation in depth. These cases suggest a gas-oil transition zone. The transition zone may extend in depth at distinguishable distances (>1 m). In a region of the transition zone a continuous vertical distribution of gas and oil, which are in thermodynamic and gravitational equilibrium, is established. Compositions, pressures and saturations of gas and oil phases are continuously varying along the geological section of the well in accordance with the equilibrium conditions.

Deposits with a long gas-oil transition zone require detailed information on the structure of this region for correct evaluation of oil and gas reserves and for a reasonable choice of development strategy.

Currently no methods exist in the practice of exploration of oil and gas deposits for determining the parameters of long gas and oil zones (distribution of gas and oil saturations along the wellbore and gas-oil capillary pressure) taking into account conditions of compositional "gas-oil" phase equilibrium.

SUMMARY

Illustrative embodiments of the present disclosure are directed to determining the mode of occurrence of gas and oil deposits, specifying geological models of these deposits and, as a consequence, a more adequate approach to the assessment of reserves and planning the development.

A method comprises taking at least one sample of a reservoir fluid from a gas part of the reservoir and at least one sample of the reservoir fluid from an oil part of the reservoir. Reservoir temperature and pressure are measured in places where the samples of the reservoir fluid are taken. And densities and compositions of the samples of the reservoir fluid are determined. The determined densities and compositions and the measured pressure and temperature are used to configure an equation of state of hydrocarbon mixtures. Porosity, water saturation, and a total hydrogen content of a saturated rock are measured along the wellbore. A volume of hydrocarbon phases is computed from the measured values of porosity and water saturation of the saturated rock, and a hydrogen content of the hydrocarbon phases is determined from the measured values of the total hydrogen content of the saturated rock. Using the equation of state of hydrocarbon mixtures density and composition of the hydrocarbon phases along the wellbore are computed. A specific hydrogen content in gas and oil along the wellbore is determined from the computed values of density and composition of the hydrocarbon phases along the wellbore. Gas and oil saturation distribution along the wellbore is determined from the determined specific hydrogen content, determined hydrogen content of the hydrocarbon phases and the measured porosity.

The densities and the compositions of the samples of the reservoir fluid are determined using standard chromatographic and fractional analysis.

The equation of state of hydrocarbon mixtures is the Peng-Robinson equation of state.

The total hydrogen content of the saturated rock along the wellbore is measured by a method of thermal neutron logging.

The porosity and the water saturation are determined by methods of acoustic, neutron and electrical logging.

From the equation of state of hydrocarbon mixtures pressure distribution in gas and oil along the wellbore is computed, and a capillary pressure curve is built on the basis of the computed pressure distributions and the determined gas and oil saturation along the wellbore.

DETAILED DESCRIPTION

Figure 1:
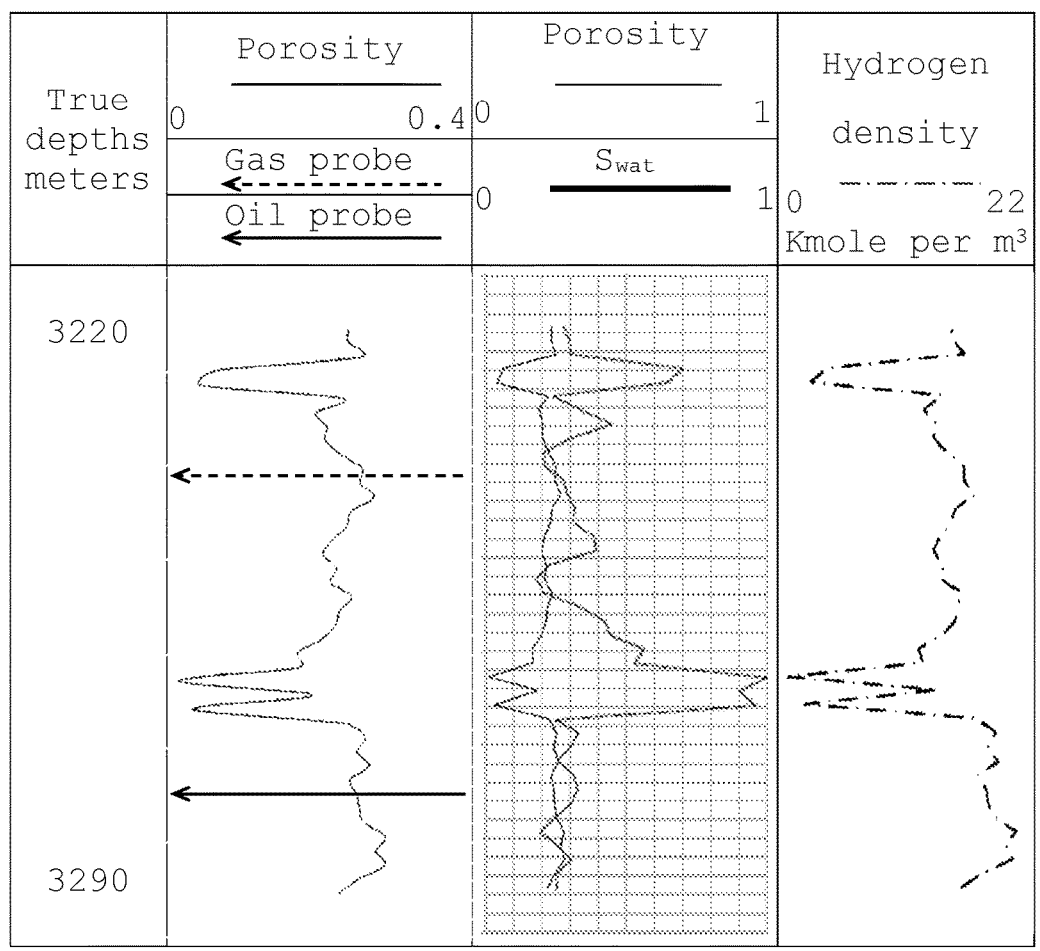
FIG. 1 shows distributions of porosity, water saturation, and hydrogen content obtained by logging methods.

The disclosed method involves the use of two sources of data (downhole samples of reservoir fluids and well logging) to obtain a GOC structure and a gas-oil capillary pressure curve in a section along a vertical or an inclined well. The downhole samples of reservoir fluids (gas, oil, water) are taken from gas and oil parts of the reservoir in conjunction with the following studies: (a) determination of reservoir thermodynamic conditions for both samples; and (b) common series of laboratory studies of PVT properties of mixtures (composition, CCE (constant composition expansion, contact condensation) and/or CVD (constant volume depletion, differential condensation)). Laboratory studies are used to configure an equation of state, i.e. to quantitatively determine free parameters in this equation, such as the Peng-Robinson equation of state (see, e.g., Firoozabadi A. Thermodynamics of Hydrocarbon Reservoirs. New York: McGraw-Hill, 1998, P. 138-143; Reid R. C., Prausnitz J. M., Poling B. E. The Properties of Gases and Liquids. New York: Mc-Graw Hill, 1987, P. 42-47; Walas S. M. Phase Equilibria in Chemical Engineering. Boston: Butterworth Publ., 1985, P. 54-57). Geophysical studies are carried out in an uncased well to determine values of porosity, water saturation, and total hydrogen content in a saturated rock against the depth along the wellbore (e.g. using a combination of acoustic, electric and radioactive logging, and analysis of mineralogical composition of rock) (see, e.g. Bassiouni Z. Theory, Measurement, and Interpretation of Well Logs. Richardson: SPE, 1994, P. 206-224; Bateman R. M. Open-Hole Log Analysis and Formation Evaluation. Boston, 1985, P. 133-146; T. Darling Well Logging and Formation Evaluation. Boston: Elsevier, 2005, P. 29-58; Ellis D. V., Singer, J. M. Well Logging for Earth Scientists. Dordrecht: Springer, 2007, P. 629-681; Tittman J. Geophysical Well Logging. Orlando: Academic Press, 1986, P. 19-57. From the data volume and hydrogen content of hydrocarbon fluids (gas and oil) along the wellbore are computed. The volume is computed from the measured values of porosity and water saturation, particularly the saturation in the hydrocarbon fluids (gas and oil) is computed from the known value of water saturation. Then, using the known value of porosity, the proportion of volume attributable to hydrocarbon fluids is computed. The hydrogen content of the hydrocarbon fluids is computed by subtraction from the total hydrogen content of the values of hydrogen content of rock and formation water computed from chemical composition (as mentioned above, mineralogical composition is assumed to be known).

Using the equation of state and the assumption of gravitational and thermodynamic (chemical) equilibrium of gas and oil phases their properties along the wellbore can be restored: (a) specific hydrogen content for separate phases and (b) pressure in phases.

Using the porosity, the saturation in the hydrocarbons, the total hydrogen content in the hydrocarbon fluids, and the specific hydrogen content in the fluids individually, it is possible to compute the distribution of saturations in gas and oil in the transition zone. Combining this distribution with pressures in the phases, it is possible to build the capillary pressure curve of the transition zone.

Consider an example of practicing the method.

Downhole samples of reservoir fluids were taken at the absolute marks of 3241 and 3276 meters in gas and oil parts of the reservoir, respectively. Corresponding measured reservoir pressures and temperatures are specified in Table 1

TABLE 1

| Formation temperature T | 76 deg. C. |
|---|---|
| Formation pressure at the mark of 3241TD | 339.6 bar |
| Formation pressure at the mark of 3276TD | 341.1 bar |

Figure 2:
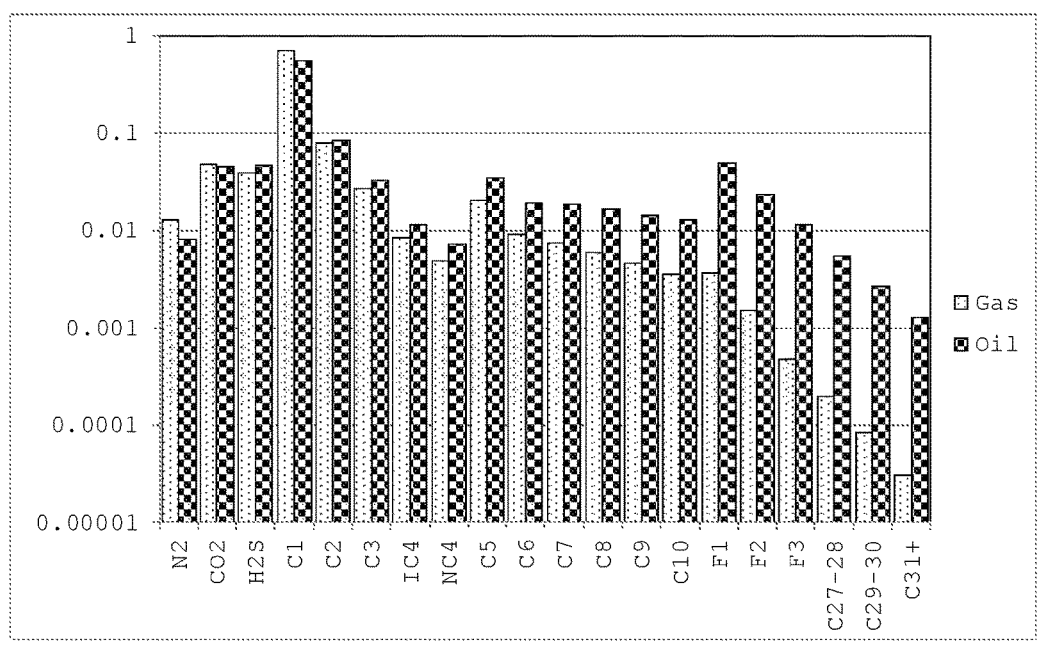
FIG. 2 shows compositions of oil and gas in obtained samples.

Table 2 and FIG. 2 show compositions of oil and gas (in mole fractions) of the obtained samples, determined by standard methods of composition determination—chromatography and fraction analysis (see, e.g. Speight J. G. Handbook of Petroleum Analysis. New York: John Wiley & Sons, 2001, P. 223-296; Speight J. G. The Chemistry and Technology of Petroleum. Boca Raton: Taylor & Francis Group, 2007, P. 177-238).

TABLE 2

|  | Gas, 3241TD | Oil, 3276TD |
|---|---|---|
| N2 | 0.013 | 0.008 |
| CO2 | 0.048 | 0.045 |

TABLE 2-continued

|  | Gas, 3241TD | Oil, 3276TD |
|---|---|---|
| H2S | 0.039 | 0.046 |
| C1 | 0.722 | 0.554 |
| C2 | 0.080 | 0.084 |
| C3 | 0.027 | 0.033 |
| IC4 | 0.008 | 0.012 |
| NC4 | 0.005 | 0.007 |
| C5 | 0.02 | 0.035 |
| C6 | 0.009 | 0.019 |
| C7 | 0.008 | 0.019 |
| C8 | 0.006 | 0.017 |
| C9 | 0.005 | 0.015 |
| C10 | 0.004 | 0.013 |
| F1 | 0.004 | 0.049 |
| F2 | 0.002 | 0.024 |
| F3 | 5E-4 | 0.012 |
| C27-28 | 2E-4 | 0.006 |
| C29-30 | 8E-5 | 0.003 |
| C31+ | 3E-5 | 1.3E-3 |

The obtained data was used to configure the Peng-Robinson equation of state, which is widely used to describe gas-liquid phase equilibrium in systems of hydrocarbons.

The following characteristics of saturated rock were obtained as a result of interpreting the data of the complex of measurements taken along the wellbore: distribution of rock composition, porosity, water saturation and total hydrogen content at absolute marks. These parameters can be determined by conventional methods using various combinations of log techniques. For example, the hydrogen content can be determined by thermal neutron logging, while the remaining parameters can be determined by a combination of acoustic, electric and other types of radioactive logging. FIG. 1 shows distributions of porosity, water saturation and hydrogen content. The water saturation is needed to estimate an actual volume attributable to hydrocarbon phases—oil and gas.

Owing to thermodynamic and gravitational equilibrium along the wellbore within a permeable rock, volatilities $f_c$ of the mixture components are varying with depth according to a specified law (1) associated with the molar weight of a component of mixture $m_c$. Using the Peng-Robinson equation of state, compositions of the hydrocarbon phases (oil and gas) at depth h can be computed from known data of the composition at depth ho. Then, the pressure in each phase (oil and gas) can be computed from the known composition and on the basis of hydrostatic equilibrium conditions. The computation is based on the following equations:

$$RT\ln\left(\frac{f_c(h_0)}{f_c^*(h)}\right) = m_c g(h_0 - h) \quad (1)$$

$$f_c^*(h) = f_c^{PR}(T, v, Z_i) \quad (2)$$

$$p(h) = p^{PR}(T, v, Z_i). \quad (3)$$

The total density of hydrogen atoms is a composite of the hydrogen content of individual phases (oil, gas, and water) with account of saturation, porosity and lithology.

$$H = \varphi(S_{wat}H_{wat} + S_{gas}H_{gas} + S_{oil}H_{oil}) + (1 - \varphi)H_{rock} \quad (4)$$

$$H_A = \sum_i N_{H_i} Z_{A_i}, A = [wat, gas, oil, rock]$$

Equations (1)-(4) use following designations: R—universal gas constant, g—acceleration of free fall, T—the temperature, v—specific volume, p—pressure, $Z_i$—composition, φ—porosity, f—volatility, S—saturation, H—total hydrogen content, $H_A$—hydrogen content of phase A, $N_{Hi}$—number of hydrogen atoms in a molecule of component i, $Z_{Ai}$—content of i-th component in phase A.

By solving equations (1)-(2) compositions of gas and oil along the wellbore are computed.

The volume attributable to the hydrocarbon phases (oil and gas) can be computed from the measured values of porosity and water saturation. The hydrogen content attributable to the hydrocarbon phases (oil and gas) can be computed from the measured values of total hydrogen content, porosity, water saturation, and hydrogen content of rock with the known lithology from equation (4) (hydrogen content of rock is determined by computations according to the known lithology and porosity. The amount of hydrogen per unit volume of the rock skeleton is determined from known chemical composition. Then, with account of known porosity, the amount of hydrogen per unit volume of rock is computed). The specific hydrogen content in gas and oil along the wellbore is computed from the composition of hydrocarbon phases against the depth along the wellbore (the amount of hydrogen per unit volume in each phase is computed from known chemical composition of phases).

Figure 3:
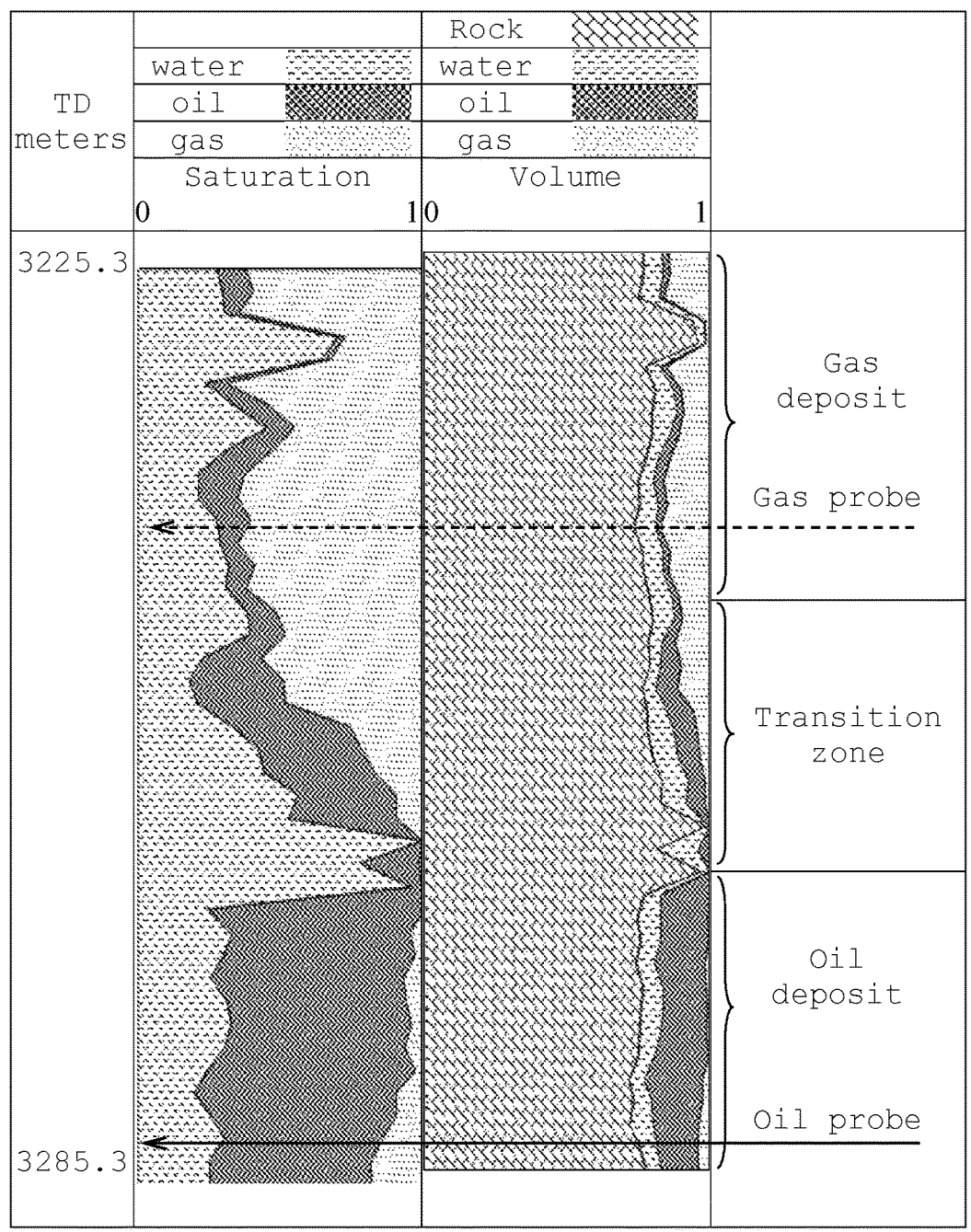
FIG. 3 shows water saturation and pore volume distributions.

The distribution of saturations in oil and gas along the well is computed from the computed specific hydrogen content in gas and oil, total hydrogen content in hydrocarbon phases, and the measured porosity of the saturated rock (relative volumetric content of oil and gas in rock can be easily estimated from known total amount of hydrogen in oil and gas, on the one hand, and specific values of the amount of hydrogen in the oil and gas separately, on the other hand). FIG. 3 shows water saturation and volume of pores determined from interpretation of the data of studying the well. Oil and gas saturations are recovered using the hydrogen content and equation (4) with computation of compositions of phases in the transition zone according to equations (1) and (2).

Figure 4:
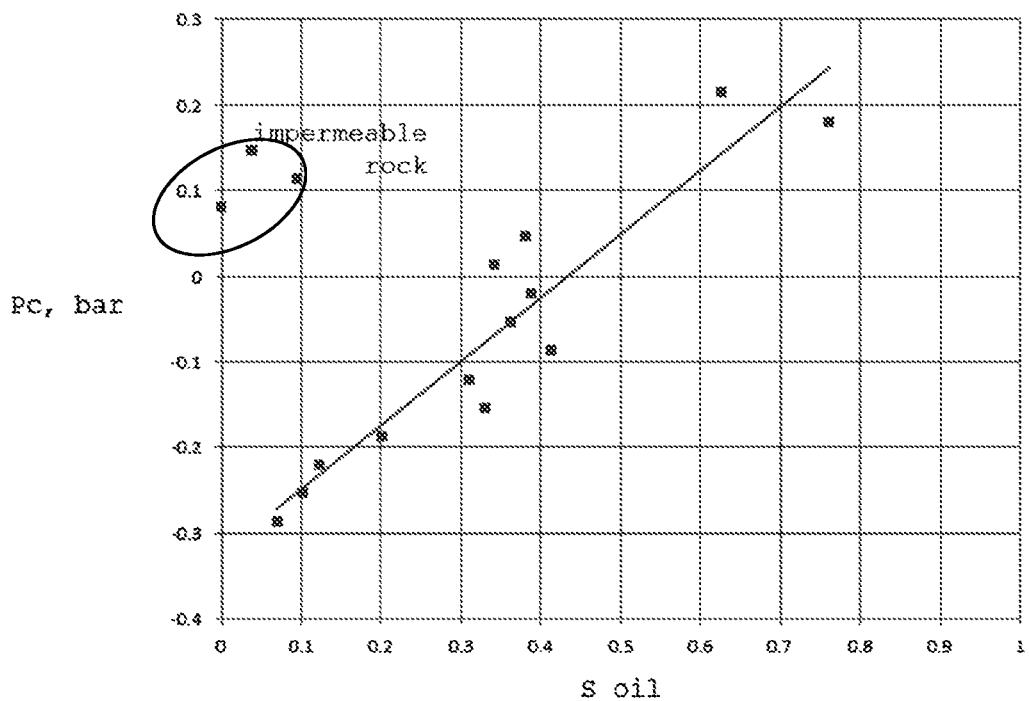
FIG. 4 is a capillary pressure curve.

Finally, knowing pressures in the phases and saturations against the depth, pressure difference in the phases versus saturation can be plotted, which is the capillary pressure curve (FIG. 4).

The invention claimed is:

1. A method for determining characteristics of a gas-oil transition zone in an uncased well drilled into a gas capped oil reservoir with a known mineralogical composition of constituent rocks, the method comprising:

taking at least one sample of a reservoir fluid from a gas part of the gas capped oil reservoir and at least one sample of the reservoir fluid from an oil part of the gas capped oil reservoir;

measuring reservoir temperature and pressure in places of the gas part and the oil part of the gas capped oil reservoir where the reservoir fluid samples are taken;

determining densities and compositions of the reservoir fluid samples taken from the gas part and the oil part of the gas capped oil reservoir;

using the determined densities and compositions of the reservoir fluid samples and the measured reservoir pressure and temperature to configure an equation of state of hydrocarbon mixtures;

measuring porosity, water saturation and total hydrogen content of a saturated rock along a wellbore;

computing a volume of hydrocarbon phases from the measured porosity and water saturation;

determining a hydrogen content of the hydrocarbon phases from the measured total hydrogen content of the saturated rock;

computing density and composition of the hydrocarbon phases along the wellbore based on gravitational and thermodynamic equilibrium of gas and oil phases and using the configured equation of state of hydrocarbon mixtures;

determining specific hydrogen content in gas and oil along the wellbore from the computed density and composition of the hydrocarbon phases along the wellbore, and determining gas and oil saturation distribution along the wellbore based on the computed specific hydrogen content in gas and oil, the determined hydrogen content of the hydrocarbon phases and the measured porosity of the saturated rock.

2. The method of claim 1, wherein the densities and the compositions of the reservoir fluid samples are determined using chromatographic and fractional analysis.

3. The method of claim 1, wherein the equation of state of the hydrocarbon mixtures is the Peng-Robinson equation of state.

4. The method of claim 1, wherein the total hydrogen content of the saturated rock along the wellbore is measured by the method of thermal neutron logging.

5. The method of claim 1, wherein the porosity and the water saturation of the saturated rock are determined by the methods of acoustic, neutron and electrical logging.

6. The method of claim 1, further comprising:

computing from the equation of state of hydrocarbon mixtures a pressure distribution in gas and oil along the wellbore, and building a capillary pressure curve on the basis of the computed pressure distribution and the determined gas and oil saturation along the wellbore.

* * * * *

UNITED STATES PATENT AND TRADEMARK OFFICE
CERTIFICATE OF CORRECTION

| | | |
|---|---|---|
| PATENT NO. | : 10,309,219 B2 | |
| APPLICATION NO. | : 15/299026 | |
| DATED | : June 4, 2019 | |
| INVENTOR(S) | : Oleg Yurievich Dinariev, Nikolay Vyacheslavovich Evseev and Evgey Nikolaevich Ivanov | |

It is certified that error appears in the above-identified patent and that said Letters Patent is hereby corrected as shown below:

On the Title Page

PLEASE ADD THE FOLLOWING:
(30)   Foreign Application Priority Data
Oct. 20, 2015   (RU) ......................2015144873

Signed and Sealed this
Fourteenth Day of June, 2022

Katherine Kelly Vidal
*Director of the United States Patent and Trademark Office*